United States Patent
Mori

(10) Patent No.: US 10,274,547 B2
(45) Date of Patent: Apr. 30, 2019

(54) MAGNETIC RESONANCE IMAGING APPARATUS INCLUDING DRAWING STRUCTURE TO DRAW ELECTRONIC APPARATUS AWAY FROM GANTRY

(71) Applicant: TOSHIBA MEDICAL SYSTEMS CORPORATION, Otawara-shi (JP)

(72) Inventor: Akio Mori, Tochigi (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 781 days.

(21) Appl. No.: 14/931,344

(22) Filed: Nov. 3, 2015

(65) Prior Publication Data
US 2016/0054399 A1    Feb. 25, 2016

Related U.S. Application Data

(63) Continuation of application No. PCT/JP2014/062892, filed on May 14, 2014.

(30) Foreign Application Priority Data

May 14, 2013   (JP) ................................. 2013-102365

(51) Int. Cl.
*G01R 33/00*   (2006.01)
*A61B 5/055*   (2006.01)
(Continued)

(52) U.S. Cl.
CPC ........ *G01R 33/0052* (2013.01); *A61B 5/0046* (2013.01); *A61B 5/055* (2013.01);
(Continued)

(58) Field of Classification Search
CPC .... G01R 33/0052; G01R 33/28; G01R 33/42; A61B 5/055; A61B 5/0046
See application file for complete search history.

(56) References Cited

U.S. PATENT DOCUMENTS 8,989,846 B2 * 3/2015 Kuduvalli ................ A61B 6/00
378/181
2002/0123682 A1 9/2002 Allred, III et al.
(Continued)

FOREIGN PATENT DOCUMENTS

JP       9-94257      4/1997
JP     2002-272703    9/2002
(Continued)

OTHER PUBLICATIONS

International Search Report for PCT/JP2014/062892, dated Jul. 29, 2014, 5 pages.
(Continued)

*Primary Examiner* — Dixomara Vargas
(74) *Attorney, Agent, or Firm* — Nixon & Vanderhye P.C.

(57) ABSTRACT

A magnetic resonance imaging apparatus according to an embodiment includes an installer provided on a gantry and configured to be capable of installing thereon an electronic apparatus. The magnetic resonance imaging apparatus according to the embodiment includes a drawing structure configured to draw out the electronic apparatus installed on the installer to a position that is away from the gantry by a certain distance in excitation of a static magnetic field magnet.

9 Claims, 4 Drawing Sheets

(51) Int. Cl.
  *G01R 33/28* (2006.01)
  *A61B 5/00* (2006.01)
  *G01R 33/42* (2006.01)
  *G01R 33/421* (2006.01)
  *G01R 33/422* (2006.01)

(52) U.S. Cl.
  CPC ............. *G01R 33/28* (2013.01); *G01R 33/42* (2013.01); *G01R 33/421* (2013.01); *G01R 33/422* (2013.01)

(56) References Cited

U.S. PATENT DOCUMENTS

| | | |
|---|---|---|
| 2010/0331667 A1 | 12/2010 | Nelson |
| 2011/0210739 A1 | 9/2011 | Ham |
| 2012/0001635 A1 | 1/2012 | Ookawa |
| 2012/0035470 A1* | 2/2012 | Kuduvalli ............... A61B 6/00 600/427 |
| 2015/0190656 A1* | 7/2015 | Kuduvalli ............... A61B 6/00 600/1 |

FOREIGN PATENT DOCUMENTS

| | | |
|---|---|---|
| JP | 2002-360534 | 12/2002 |
| JP | 2008-307309 | 12/2008 |
| JP | 2011-512930 | 4/2011 |
| JP | 2012-030051 | 2/2012 |
| JP | 2012-507329 | 3/2012 |
| WO | WO 2010/052616 | 5/2010 |

OTHER PUBLICATIONS

Written Opinion of the ISA for PCT/JP2014/062892, dated Jul. 29, 2014, 4 pages.

* cited by examiner though it's a magnetic resonance imaging apparatus.

MAGNETIC RESONANCE IMAGING APPARATUS INCLUDING DRAWING STRUCTURE TO DRAW ELECTRONIC APPARATUS AWAY FROM GANTRY

CROSS-REFERENCE TO RELATED APPLICATIONS

This application is a continuation of PCT international application Ser. No. PCT/JP2014/062892 filed on May 14, 2014 which designates the United States, incorporated herein by reference, and which claims the benefit of priority from Japanese Patent Application No. 2013-102365, filed on May 14, 2013, the entire contents of which are incorporated herein by reference.

FIELD

Embodiments described herein relate generally to a magnetic resonance imaging apparatus.

BACKGROUND

Magnetic resonance imaging is an imaging method of magnetically exciting atomic nucleus spins of a subject placed in a static magnetic field with a radio frequency (RF) pulse of a Larmor frequency and generating an image based on data of magnetic resonance signals generated with the excitation. The magnetic resonance imaging is performed by a magnetic resonance imaging apparatus (hereinafter, referred to as "MRI apparatus" appropriately).

Conventionally, components of the MRI apparatus are installed in an imaging room, a machine room, an operation room, and the like in a dispersed manner in accordance with types of the components. Shield is applied to the wall surfaces of the imaging room, and a gantry including a static magnetic field magnet, a gradient coil, a radio frequency (RF) transmitting coil, and a couch is installed in the imaging room. On the other hand, other components are installed in the machine room and the operation room. For example, several components such as a gradient power supply, a gradient amplifier, an RF transmitter, and an RF transmission amplifier are installed in the machine room. Depending on installation environments of the MRI apparatus, a space for the machine room or the like cannot be ensured sufficiently in some cases.

DETAILED DESCRIPTION

A magnetic resonance imaging apparatus according to an embodiment includes an installer provided on a gantry and configured to be capable of installing thereon an electronic apparatus. The magnetic resonance imaging apparatus according to the embodiment includes a drawing structure configured to draw out the electronic apparatus installed on the installer to a position that is away from the gantry by a certain distance in excitation of a static magnetic field magnet.

Hereinafter, an MRI apparatus according to embodiments will be described with reference to the drawings. It should be noted that the embodiments are not limited to the following embodiments. Contents that will be described in the embodiments can be applied to other embodiments in the same manner in principle.

First Embodiment

Figure 1:
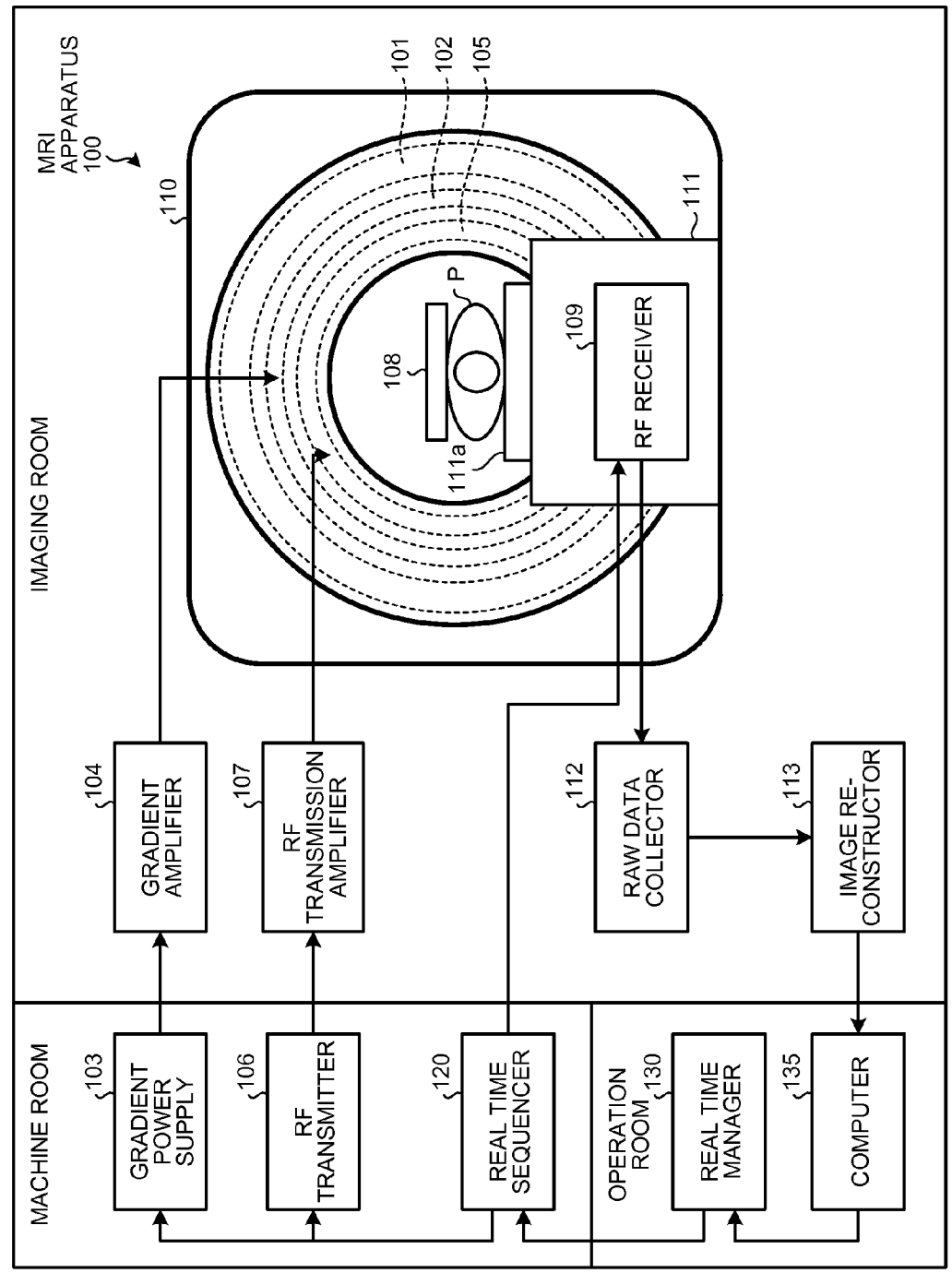
FIG. 1 is a functional block diagram illustrating the configuration of an MRI apparatus according to a first embodiment.

FIG. 1 is a functional block diagram illustrating the configuration of an MRI apparatus 100 in a first embodiment. As illustrated in FIG. 1, the MRI apparatus 100 includes a static magnetic field magnet 101, a gradient coil 102, a gradient power supply 103, a gradient amplifier 104, an RF transmitting coil 105, an RF transmitter 106, an RF transmission amplifier 107, an RF receiving coil 108, and an RF receiver 109. The MRI apparatus 100 includes a couch 111, a raw data collector 112, an image reconstructor 113, a real time sequencer 120, a real time manager 130, and a computer 135. Hereinafter, as illustrated in FIG. 1, among the components of the MRI apparatus 100, a housing including the static magnetic field magnet 101, the gradient coil 102, and the RF transmitter 106 is referred to as a gantry 110. The MRI apparatus 100 does not include a subject P (for example, human body). The configuration as illustrated in FIG. 1 is merely an example. The parts may be integrated or separated appropriately.

The static magnetic field magnet 101 is a magnet formed into a hollow cylindrical shape and generates a static magnetic field in a space in the cylinder. The static magnetic field magnet 101 is a superconducting magnet, for example, and is excited upon reception of supply of electric current from a static magnetic field power supply (not illustrated). The static magnetic field magnet 101 may be a permanent magnet and in this case, the MRI apparatus 100 may not include the static magnetic field power supply. Furthermore, the static magnetic field power supply may be provided separately from the MRI apparatus 100.

The gradient coil 102 is a coil arranged at the inner side of the static magnetic field magnet 101 and formed into a hollow cylindrical shape. The gradient coil 102 receives supply of current from the gradient amplifier 104 and generates a gradient magnetic field. The gradient power supply 103 generates the current that is supplied to the gradient coil 102 in accordance with a control signal from the real time sequencer 120. The gradient amplifier 104 amplifies the current generated by the gradient power supply 103 and supplies it to the gradient coil 102.

The RF transmitting coil 105 is arranged at the inner side of the gradient coil 102. The RF transmitting coil 105 receives supply of an RF pulse from the RF transmission amplifier 107 and generates a high-frequency magnetic field. The RF transmitter 106 generates the RF pulse that is supplied to the RF transmitting coil 105 in accordance with a control signal from the real time sequencer 120. The RF transmission amplifier 107 amplifies the RF pulse generated by the RF transmitter 106 and supplies it to the RF transmitting coil 105.

The RF receiving coil 108 receives a magnetic resonance signal (hereinafter, referred to as "MR signal") emitted from the subject P by influence of the high-frequency magnetic field and outputs the received MR signal to the RF receiver 109.

The combination of the RF transmitting coil 105 and the RF receiving coil 108 as described above is merely an example. It is sufficient that the RF coil is configured by one of a coil having only a transmission function, a coil having only a reception function, and a coil having transmission and reception functions, or by two or more of these coils in combination.

The RF receiver 109 detects the MR signal that is output from the RF receiving coil 108 and generates MR data (hereinafter, referred to as "raw data" appropriately) based on the detected MR signal. To be specific, the RF receiver 109 processes by digital conversion the MR signal that is output from the RF receiving coil 108 so as to generate the raw data. The RF receiver 109 transmits the generated raw data to the raw data collector 112. For example, the RF receiver 109 is implemented in the couch 111.

The couch 111 includes a couchtop 111a on which the subject P is placed. Normally, the couch 111 is installed such that a center axis of the cylinder of the static magnetic field magnet 101 and the lengthwise direction of the couch 111 are parallel with each other. The couchtop 111a can be moved in the lengthwise direction and the up-down direction and is inserted into the space in the cylinder at the inner side of the RF transmitting coil 105 in a state where the subject P is placed on the couchtop 111a.

The raw data collector 112 performs pieces of correction processing such as averaging processing, phase correction processing, and rearrangement processing on the raw data transmitted from the RF receiver 109 and transmits the raw data after correction to the image reconstructor 113. The image reconstructor 113 performs pieces of image processing such as Fourier transform and image filtering on the raw data transmitted from the raw data collector 112 so as to reconstruct two-dimensional or three-dimensional image data, and transmits the reconstructed image data to the computer 135.

The real time sequencer 120 drives the gradient power supply 103, the RF transmitter 106, and the RF receiver 109 based on a data sequence that is transmitted from the real time manager 130 so as to image the subject P. The real time manager 130 analyzes imaging conditions that are transmitted from the computer 135 and generates the data sequence necessary for an operation of the real time sequencer 120. In this data sequence, intensity and a supply timing of the current that is supplied to the gradient coil 102, intensity and an application timing of the RF pulse that is supplied to the RF transmitting coil 105, a detection timing of the MR signal, and the like are defined.

All of the above-mentioned units, the real time sequencer 120, the real time manager 130, and the like are electronic apparatuses and include an integrated circuit such as an application specific integrated circuit (ASIC) and a field programmable gate array (FPGA) or an electronic circuit such as a central processing unit (CPU) and a micro processing circuit (MPU).

The computer 135 controls the entire MRI apparatus 100. For example, the computer 135 includes a controller, a storage, an input circuitry, and a display. The controller is an integrated circuit such as an ASIC and an FPGA or an electronic circuit such as a CPU and an MPU. The storage is a semiconductor memory element such as a random access memory (RAM) and a flash memory, a hard disk, an optical disk, or the like. The input circuitry is a pointing device such as a mouse and a track ball or an input device such as a keyboard. The display is a display device such as a liquid crystal display.

In the first embodiment, as illustrated in FIG. 1, the gradient amplifier 104, the RF transmission amplifier 107, the raw data collector 112, and the image reconstructor 113 are installed in the imaging room. To be specific, these units are installed on an installer (hereinafter, referred to as accommodation case) provided along the side surface of the gantry 110.

Figure 2A:
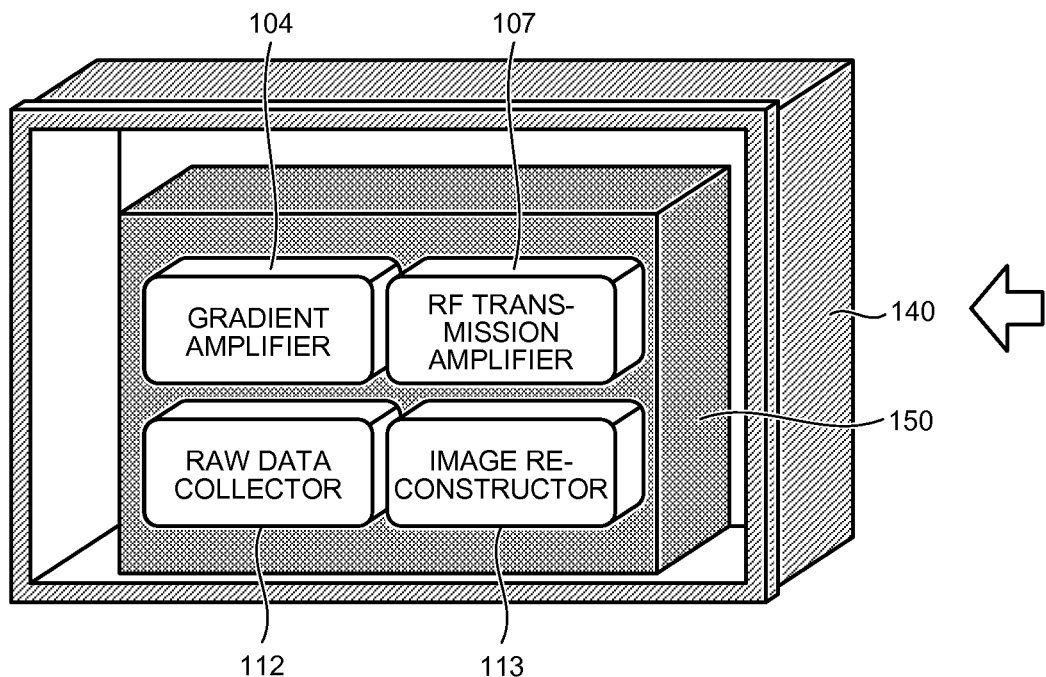
FIGS. 2A and 2B are views for explaining an accommodation case in the first embodiment.
Figure 2B:
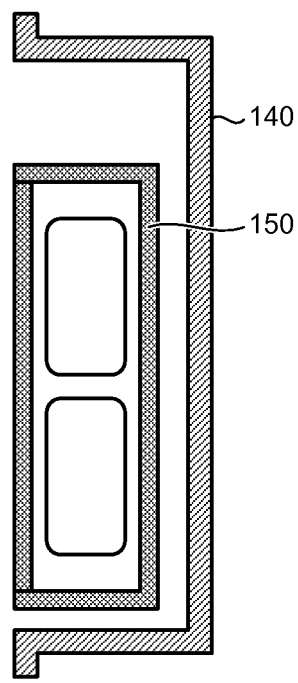

FIGS. 2A and 2B are views for explaining the accommodation case in the first embodiment. FIG. 2A is a perspective view of the accommodation case and FIG. 2B is a sectional view when seen from an outlined arrow in FIG. 2A. As illustrated in FIGS. 2A and 2B, the accommodation case in the first embodiment has a dual configuration with a magnetic shield case 140 for blocking a magnetic field and an RF shield case 150 for blocking high-frequency electromagnetic waves. That is to say, the units are accommodated in the RF shield case 150 first. Then, the RF shield case 150 is accommodated in the magnetic shield case 140.

The magnetic shield case 140 mainly plays a role in blocking influence of a strong magnetic field that is generated on the gantry 110 so as to protect circuits of the units accommodated in the magnetic shield case 140. On the other hand, the RF shield case 150 mainly plays a role in preventing electromagnetic waves from the circuits of the units accommodated in the RF shield case 150 from transmitting to the gantry 110 side as noise or conversely preventing electromagnetic waves from the gantry 110 side from transmitting to the circuits of the units as noise during imaging.

Furthermore, in the first embodiment, the magnetic shield case 140 has a configuration in which the side surface at the opposite to the side surface at the gantry 110 side is opened as illustrated in FIG. 2B. Thus, the magnetic shield case 140 can have a configuration in which one surface is opened. The RF shield case 150 has a sealed configuration as illustrated in FIG. 2B. The sealed configuration of the RF shield case 150 provides two aspects; that is, an aspect in which operation clock noise therein is not leaked to the outside so as not to influence imaging and an aspect in which malfunction by influence of an RF pulse or a gradient pulse from a system does not occur during the imaging. The magnetic shield case 140 and the RF shield case 150 are different in material in addition to the above-mentioned configuration. An exclusive material for blocking the influence of the strong magnetic field is used for the magnetic shield case 140. For example, an oriented electromagnetic steel sheet having high magnetic permeability, a non-oriented electromagnetic steel sheet, permalloy, a soft magnetic steel sheet, amorphous, a microcrystalline magnetic material formed by crystallizing a quenched liquid thin belt, or the like is used therefor.

All of the above-mentioned units have a configuration covered with metal and are heavy objects in many cases. In the case where the units are accommodated in the accommodation case as illustrated in FIGS. 2A and 2B and are installed along the side surface of the gantry 110, for example, when these units are taken out to the outside of the accommodation case for adjustment, exchange of parts, or the like, there is a risk that they receive suction force of the magnetic field and are attracted to the gantry 110 side with strong force. As one method for avoiding the risk, it is suggested that the static magnetic field magnet 101 is demagnetized before the adjustment, the exchange of parts, or the like is performed. The demagnetization, however, takes much time and consumes helium gas, which is largely disadvantageous.

The first embodiment proposes a structure capable of handling these units under an environment where excitation of the static magnetic field magnet 101 is kept without demagnetization in the case of the adjustment, the exchange of parts, or the like. To be specific, in the first embodiment, a structure that is capable of drawing out only the RF shield case 150 from the accommodation case to a constant distance from the gantry 110 safely and easily is provided. In this case, the operation such as the adjustment and the exchange of parts is performed at a position that is away from the gantry 110 by the constant distance.

Figure 3A:
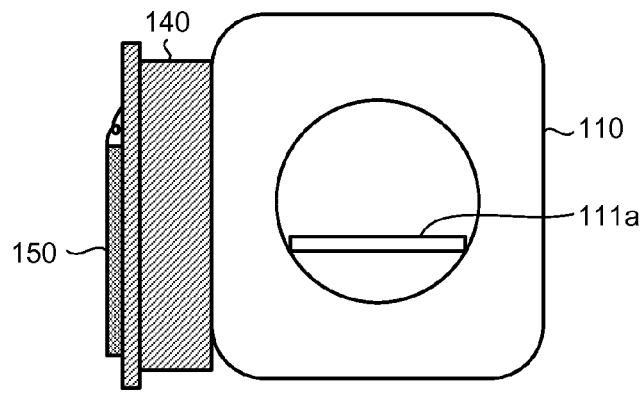
FIGS. 3A to 3C are views for explaining a drawing structure in the first embodiment.
Figure 3B:
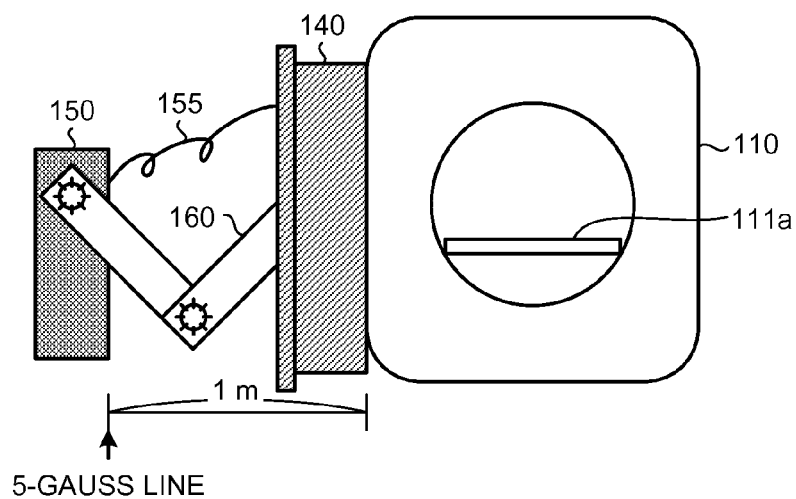
Figure 3C:
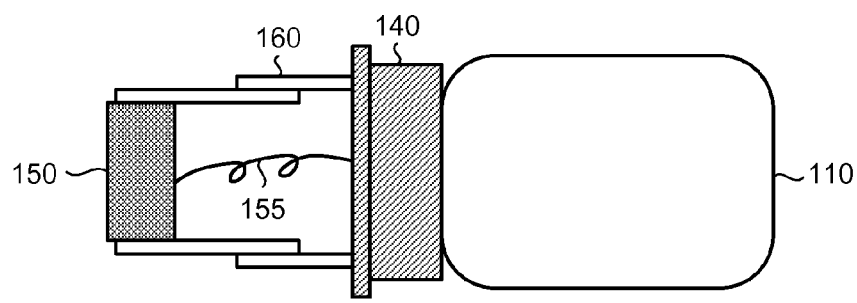

FIGS. 3A to 3C are views for explaining the drawing structure in the first embodiment. FIG. 3A illustrates a state where the RF shield case 150 is accommodated in the magnetic shield case 140 installed along the side surface of the gantry 110. FIGS. 3A to 3C illustrate a state where the RF shield case 150 slightly protrudes from the magnetic shield case 140 for the convenience of explanation but the embodiment is not limited thereto and the RF shield case 150 may be completely accommodated in the magnetic shield case 140. FIG. 3B illustrates a state where the RF shield case 150 has been drawn out from the magnetic shield case 140. FIG. 3C is a view when the state of FIG. 3B is seen from the upper side of the gantry 110. FIGS. 3A to 3C illustrate a state where the RF shield case 150 is drawn out with cables 155 of the units in the RF shield case 150 connected to the respective units.

The constant distance from the gantry 110 is a distance by which the suction force of the magnetic field is sufficiently reduced in the operation such as the adjustment and the exchange of parts and is a distance to a 5-gauss line or a 10-gauss line as illustrated in FIG. 3B, for example. The distance can be calculated when the static magnetic field magnet 101 is designed and so on. The drawing structure is therefore designed so as to enable drawing to at least the distance safely and easily.

The safe drawing does not indicate such a structure that is attracted easily with the suction force from the gantry 110 side during the drawing to the constant distance; instead, it indicates such a structure having a constant rigidity against the suction force. The rigidity may simply mean rigidity in which a certain force is required for movement or the rigidity may be applied by a lock structure that restricts movement in a suction direction of the magnetic field. Furthermore, the simple drawing indicates that a drawing operation and a return operation to the accommodation case can be made by only a manual operation of turning a handle with light force, for example.

In order to provide the safe and simple drawing structure, an extension structure 160 as illustrated in FIG. 3B is proposed in the first embodiment. For example, the extension structure 160 is configured by overlapping rectangular plate-like parts with each other on respective end portions and bonding them in a rotatable manner so as to be closed and opened at desired angles. The extension structure 160 can extend and be shortened by alternately coupling the parts by the number thereof in accordance with the distance to each other. It should be noted that there are similar structures called a magic hand configuration, an expand configuration, and the like.

In the first embodiment, the extension structure 160 is designed such that the parts are bonded with constant rigidity against the suction force. For example, a configuration in which required force is different depending on rotating directions may be employed as follows. That is, the parts extend with relatively small force in the direction of being drawn out from the gantry 110 side whereas the parts are shortened only when relatively large force is applied in the accommodation direction into the accommodation case.

A lock structure may be configured with which, when the parts are opened to a certain angle to each other, for example, they are once fixed at the angle so as not to further extend or be shortened. For example, the configuration is employed in which, when an angle between the two parts reaches the certain angle in the extension structure 160, the two parts are fixed at the angle and do not return in the accommodation direction easily. Subsequently, when the RF shield case 150 is drawn out, an angle between the following folded parts is gradually opened. Then, when an angle between the parts reaches the certain angle again, the two parts are fixed at the angle and do not return in the accommodation direction easily. Thus, the parts are fixed in a stepwise manner, so that the RF shield case 150 can be drawn out safely.

Furthermore, as for the constant distance from the gantry 110, for example, some mark may be put on a floor surface in the imaging room and a user may draw out the RF shield case 150 to a position thereof while checking the mark. Alternatively, a configuration enabling the user to recognize that the RF shield case 150 has reached a fixed position with an action of some kind of lock structure when the extension structure 160 has extended to the safe distance (for example, a configuration in which the extension structure 160 becomes incapable of extending with a clicking sound) may be employed. On the other hand, when the RF shield case 150 is accommodated in the magnetic shield case 140, a configuration that becomes capable of moving in the accommodation direction by releasing the lock structure, for example, may be employed.

In the first embodiment, a configuration causing the RF shield case 150 to return to the same position as the position at which it has been installed before being drawn when the RF shield case 150 drawn out from the magnetic shield case 140 is accommodated in the magnetic shield case 140 again is provided. For example, a configuration enabling the user to recognize accommodation at a fixed position (for example, a configuration in which the RF shield case 150 becomes incapable of moving with a clicking sound) may be employed. A configuration fixing the RF shield case 150 to the magnetic shield case 140 with pins, screws, or the like may be employed, for example.

The RF shield case 150 is made to return to the original position with high reproducibility, thereby keeping the states of the magnetic field before the drawing and after the drawing to be the same. In other words, the magnetic field that is uniformly kept at the position before the drawing can be kept in the same manner even after the units are once drawn out and returned.

Furthermore, also in order not to transmit vibration from the gantry 110 during the imaging, the configuration fixing the RF shield case 150 to the magnetic shield case 140 fixed to the gantry 110 with pins, screws, or the like may be employed. It should be noted that the configuration preventing vibration from transmitting to the units is not limited thereto. For example, the units may be fixed with pins, screws, or the like in the RF shield case 150. Alternatively, vibration at the gantry 110 side may be made difficult to transmit by providing a buffer material between the gantry 110 and the magnetic shield case 140, for example. These methods may be selected or combined appropriately.

The above-mentioned extension structure 160 is merely an example. For example, the extension structure 160 is not limited to have the configuration of two rows as illustrated in FIGS. 3A to 3C and may have a configuration of one now. Furthermore, for example, the extension structure 160 may have a rhombic configuration or a configuration using a rhombic shape in the horizontal direction. It is sufficient that the form, the number, and the like thereof are selected appropriately in accordance with a relation between suction force and a target to be drawn out.

As described above, in the first embodiment, the units installed in the machine room conventionally can be installed in the imaging room, thereby saving a space of the machine room and saving an entire space that is used for installation of the MRI apparatus 100.

In particular, a large advantageous effect is provided for units having relatively large sizes such as the gradient amplifier 104 and the RF transmission amplifier 107. The gradient amplifier 104 and the RF transmission amplifier 107 use relatively thick cables. Accordingly, capability of installation of these units at positions adjacent to the gantry 110 can shorten laying distances of the cables and eventually, can reduce loss of signals.

In addition, as described above, in the first embodiment, the safe and simple drawing structure is provided, which ensures the distance from the side surface of the gantry 110 without demagnetization, and is advantageous in operation efficiency and cost. For example, capability of drawing out of the units while connection to a power supply is kept can enable adjustment such as checking of an LED and exchange of the parts in a state close to actual configurations.

The RF shield case 150 itself is drawn out, thereby drawing out the units with a simple operation without detaching and attaching the units themselves, detaching screws, and so on.

Second Embodiment

Subsequently, a second embodiment will be described. In the second embodiment, a slide structure 170 is proposed as an example of the drawing structure. Other points are the same as those of the MRI apparatus 100 as described in the first embodiment in principle.

Figure 4A:
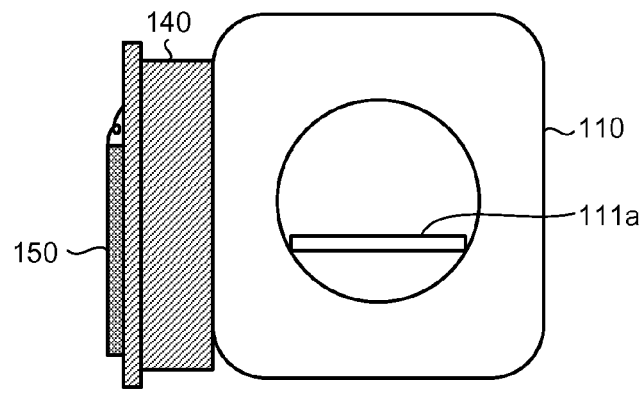
FIGS. 4A to 4C are views for explaining a drawing structure according to a second embodiment.
Figure 4B:
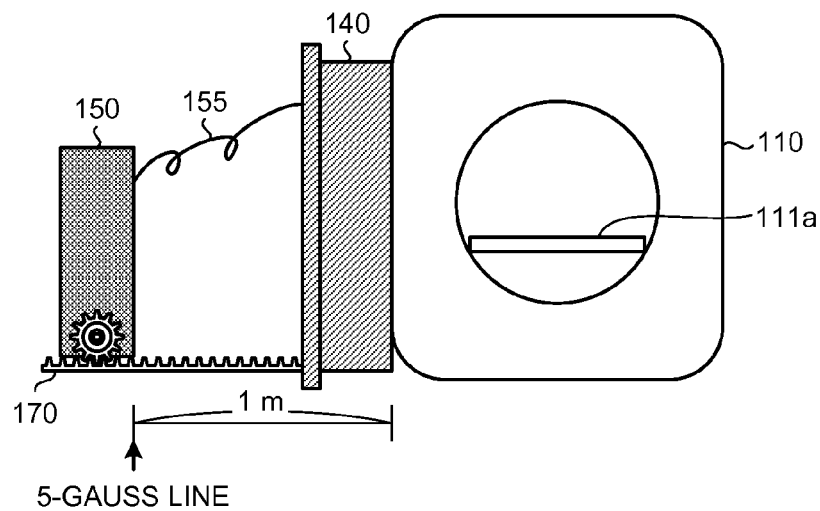
Figure 4C:
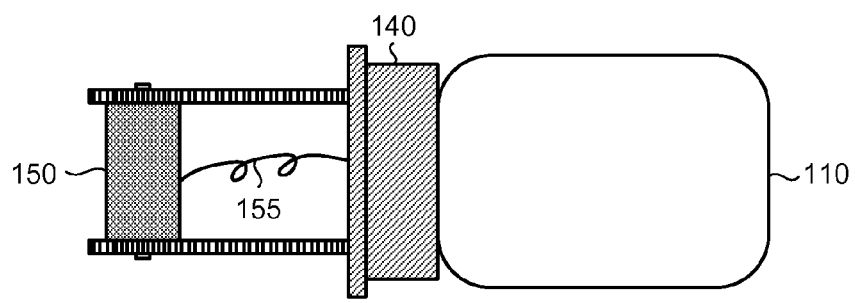

FIGS. 4A to 4C are views for explaining the drawing structure in the second embodiment. For example, the slide structure 170 includes two rails as illustrated in FIGS. 4B and 4C and the RF shield case 150 with gears move on the rails in a sliding manner.

In the second embodiment, the slide structure 170 is designed such that the movement has constant rigidity against the suction force. For example, as illustrated in FIG. 4B, a configuration may be employed in which gear cutting is applied on the rails so that the RF shield case 150 does not move easily unless a certain force is applied. This configuration may employ a structure with which a certain force is applied with the principle of leverage only when a handle operation is made, so that the RF shield case 150 moves, for example.

Alternatively, for example, when the RF shield case 150 is drawn out in the drawing direction and the user releases the handle, a lock structure (for example, a lock plate) incorporated in the RF shield case 150 or the rails may arise so as to function as a stopper preventing the RF shield case 150 from moving in the suction direction.

In the same manner as the first embodiment, the user may directly hold the RF shield case 150 and draw out the RF shield case 150 from the magnetic shield case 140 or may manually turn a handle (not illustrated) attached to the magnetic shield case 140, the RF shield case 150, or the like and draw out the RF shield case 150.

The rails of the slide structure 170 may be configured to be accommodated in the magnetic shield case 140 by being folded and shortened in a stepwise manner, or may be configured to be accommodated in the magnetic shield case 140 by setting installation positions of the rails themselves to heights to some extent and folding the rails downward from bonding portions on halfway.

Other Embodiments

Embodiments are not limited to the above-mentioned embodiments.

Although four units including the gradient amplifier, the RF transmission amplifier, the raw data collector, and the image reconstructor are installed in the imaging room in the above-mentioned embodiments, the embodiments are not limited thereto. Units that are installed in the imaging room can be optionally selected. For example, the gradient power supply and the RF transmitter may be installed in the imaging room or the raw data collector and the image reconstructor may be installed in the machine room. Furthermore, a computer can be also installed in the imaging room as long as the computer is a disk or the like made of silicon.

Furthermore, there are the cases where the machine room itself cannot be provided and the case where the machine room can be provided but a space therefor is small. The same holds true for the operation room. That is to say, an example of dispersed arrangement as illustrated in FIG. 1 is merely an example, and combinations of units to be installed and rooms therefor can be optionally changed in accordance with an environment in which the MRI apparatus is installed. Furthermore, segmentation of the units, names of the units, names of the parts, and the like can be optionally changed.

Cable

In the above-mentioned embodiments, the RF shield case 150 is drawn out while connection of the cables of the units to the respective units is kept. The gradient amplifier 104 and the RF transmission amplifier 107 use relatively thick cables and in this case, attachment and detachment structures capable of attaching and detaching the cables easily may be provided. For example, it is sufficient that when the RF shield case 150 is drawn out from the magnetic shield case 140, the cables are detached. Alternatively, for example, conduction structures such as wiring bus bars made of metal may be provided on the rails themselves in the slide structure 170 as described in the second embodiment.

Accommodation Case

The accommodation case as described in the above-mentioned embodiments is merely an example. For example, the accommodation case may be configured as one shield case serving as the magnetic shield case and the RF shield case. As described above, however, the RF shield case should have the sealed configuration. When one shield case serving as the magnetic shield case and the RF shield case is used, the shield case is required to be made of material that is used exclusively for the magnetic shield case and have the sealed configuration.

Integration

Although the magnetic shield case 140 is installed along the side surface of the gantry 110 in the above-mentioned embodiments, the embodiments are not limited thereto. The gantry 110 and the magnetic shield case 140 may be integrated. For example, the following configuration may be employed: the magnetic shield case 140 itself is accommodated in a cover of the gantry 110, and when the cover of the gantry 110 (for example, a side cover) is detached, the magnetic shield case 140 and the RF shield case 150 installed therein can be handled.

The magnetic resonance imaging apparatus according to one or more of the above-mentioned embodiments achieves space saving.

While certain embodiments have been described, these embodiments have been presented by way of example only, and are not intended to limit the scope of the inventions.

Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) apparatus comprising:
    an MRI gantry including a static magnetic field magnet configured to generate a static magnetic field for MRI when excited;
    an MRI electronic system component installer provided on the gantry and configured to be capable of installing thereon MRI electronic system component apparatus; and
    a drawing structure configured to draw out the MRI electronic system component apparatus installed on the installer to a position that is away from the gantry by a predetermined distance while the static magnetic field magnet remains in in an excited state.

2. The magnetic resonance imaging apparatus according to claim 1, wherein the predetermined distance is a distance at which attractive suction force of a magnetic field, generated by the static magnetic field magnet when in an excited state, is reduced to a predetermined value.

3. The magnetic resonance imaging apparatus according to claim 1, wherein the drawing structure draws out the MRI electronic system component apparatus by a manual operation.

4. The magnetic resonance imaging apparatus according to claim 1, wherein the drawing structure re-installs the MRI electronic system component apparatus to a position same as a position at which the MRI electronic system component apparatus had been installed before being drawn away from the gantry.

5. The magnetic resonance imaging apparatus according to claim 1, wherein the MRI electronic system component apparatus is fixed to and installed on the installer or the drawing structure when the MRI electronic system component apparatus is installed on the installer.

6. The magnetic resonance imaging apparatus according to claim 1, wherein the installer comprises a shield case made of material that blocks electromagnetic waves and is capable of accommodating the MRI electronic system component apparatus.

7. The magnetic resonance imaging apparatus according to claim 6, wherein
    (a) the shield case has a dual configuration with a first shield case, one surface of which is open, and a second shield case accommodated in the first shield case and sealed, and
    (b) the drawing structure draws out the MRI electronic system component apparatus accommodated in the second shield case together with the second shield case.

8. The magnetic resonance imaging apparatus according to claim 1, wherein the drawing structure includes a lock structure restricting movement of the MRI electronic system component apparatus in an attractive suction direction of a magnetic field generated by said static magnetic field magnet when in an excited state, said attractive suction direction being opposite to a drawing direction.

9. The magnetic resonance imaging apparatus according to claim 1, wherein the MRI electronic system component apparatus is at least one of (a) a gradient amplifier amplifying electric current that is supplied to an MRI gradient coil located in the gantry, (b) a radio frequency (RF) transmission amplifier amplifying current that is supplied to an MRI RF transmitting coil, (c) a raw MRI data collector collecting raw MRI data, and (d) an MR image reconstructor reconstructing an MR image from the raw MRI data.

* * * * *